US006849435B2

(12) United States Patent
Lechelt-Kunze et al.

(10) Patent No.: US 6,849,435 B2
(45) Date of Patent: Feb. 1, 2005

(54) USE OF VLCFAE FOR IDENTIFYING HERBICIDALLY ACTIVE COMPOUNDS

(75) Inventors: Christa Lechelt-Kunze, Köln (DE); Ruth Meissner, Leverkusen (DE); Klaus Tietjen, Langenfeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 3 days.

(21) Appl. No.: 09/905,657

(22) Filed: Jul. 13, 2001

(65) Prior Publication Data

US 2002/0038471 A1 Mar. 28, 2002

(30) Foreign Application Priority Data

Jul. 18, 2000 (DE) ......................................... 100 34 804

(51) Int. Cl.$^7$ ............................. C12N 9/00; C12N 9/88; C12N 5/04; A01H 1/00; C07H 21/04
(52) U.S. Cl. ....................... 435/183; 435/232; 435/419; 435/69.2; 800/281; 800/298; 536/23.2; 536/23.6
(58) Field of Search ................................. 435/183, 232, 435/419, 69.2; 800/281, 298; 536/23.2, 23.6

(56) References Cited

U.S. PATENT DOCUMENTS 6,307,128 B1 * 10/2001 Jaworski et al. ............ 800/281

FOREIGN PATENT DOCUMENTS

| WO | 95/15387 | 6/1995 |
| WO | 96/13582 | 5/1996 |
| WO | 98/46766 | 10/1998 |
| WO | 98/54954 | 12/1998 |
| WO | 00/08172 | 2/2000 |

OTHER PUBLICATIONS

Sequence alignment between Accession No. 064846 and Applicants Seq Id No.: 2.*
The Plant Cell 11, (month unavailable), 1999, pp. 2187–2201, A. Yephremov et al, "Characterization of the FIDDLEHEAD Gene of Arabidopsis Reveals a Line Between Adhesion Response and Cell Differentiation in the Epidermis".
BioTechniques 8, (month unavailable), 1990, pp. 148–149, C. Puissant et al, "An Improvement of the Single–Step Method of the RNA Isolation by Acid Guanidinium Thiocyanate–Phenol–Chloform Extraction".
Development Biology, 152, (month available), 1992, pp. 383–392, S. J. Lolle et al, "Fiddlehead: An ArabidopsisMutant Constitutively Expressing an Organ Fusion Program That Involves Interactions Between Epidermal Cells".

PNAS 97(3), (month unavailable), 2000, pp. 1311–1316, R. E. Pruitt et al, "FIDDLEHEAD", a Gene Required to Suppress Epidermal Cell Interactions in Arabidopsis, Encldes a Putative Lipid Biosynthesis Enzyme.
Gene, 156, (month unavailable) 1995, pp. 119–122, D. Mumberg et al, "Yeast Vectors for the Controlled Expression of Heterologous Proteins in Different Genetic Backgrounds".
J. Plant Physiol. 144, (month unavailable) 1994, pp. 376–384, C. Möllers et al, "Screening Herbicide Effects on Lipid Metabolism of Storage Lipids by In Vitro Culture of Microspore–Derived Embryoids of Brassica Napus ".
The Plant journal 2(3), (month unavailable) 1992, pp. 417–422, M.Minet et al, "Complementation of Saccharomyces Cerevisiae Auxotrophic Mutants by Arabidopsis Thaliana cDNAs".
The Plant Journal 12(1), (month unavailable) 1997, pp. 121–131, A. A. Millar et al, "Very–Long–Chain Fatty Acid Biosynthesis is Controlled Through the Expression and Specificity of the Condensing Enzyme".
Z. Naturforsch., 53c, (month unavailable) 1998, pp. 1004–1011, B. Matthes et al, "Chloracetamide Mode of Action II: Inhibition of Very Long Chain Fatty Acid Synthesis in Higher Plants".
Trends in Plant Science 5, (month unavailable) 2000, pp. 95–101, A. A. Millar et al, "All Fatty Acids Are Not Equal: Discrimination In Plant Membrane Lipids".
Spektrum Akademischer Verlag, Heidelberg, Berlin, (month unavailable) 1998, F. Lottspeich et al (editors) "Bioanalytik".
Pest Management Science 56, (month unavailable) 2000, pp. 497–508, P. Böger et al, "Towards the Primary Target of Chloroacetamides—New Findings Pave the Way".
Nucl. Acids Res. 12(22), (month unavailable) 1984, M. Bevan, "Binary Agrobacterium Vectors for Plant Transformation".
Arabidopsis Protocols, edited by Martinez–Zapater J. M. und Salinas, J., (month unavailable) 1998, pp. 259–266, Humana Press ISBN 0–89603–391–0.
Nucleic Acids Research, vol. 25, No. 17, (month unavailable) 1997, pp. 3389–3402, S. F. Altschul et al, "Gapped BLAST and PSI–BLAST: A New Generation of Protein Database Search Programs".
Phytochemistry 30(5), (month unavailable) 1991, pp. 1445–1447, K. O. Abulnaja et al, "Thiocarbamate Herbicides Inhibit Fatty Acid Elongation in a Variety of Monocotyledons".

(List continued on next page.)

Primary Examiner—Tekchand Saidha
(74) Attorney, Agent, or Firm—Richard E. L. Henderson; Raymond J. Harmuth

(57) ABSTRACT

The invention relates to the use of nucleic acids which code for plant polypeptides with the biological activity of very long chain fatty acid elongases and to the use of the polypeptides encoded thereby for identifying novel, herbicidally active compounds, and to methods for finding modulators of these polypeptides.

5 Claims, 1 Drawing Sheet

OTHER PUBLICATIONS

Figure 1:
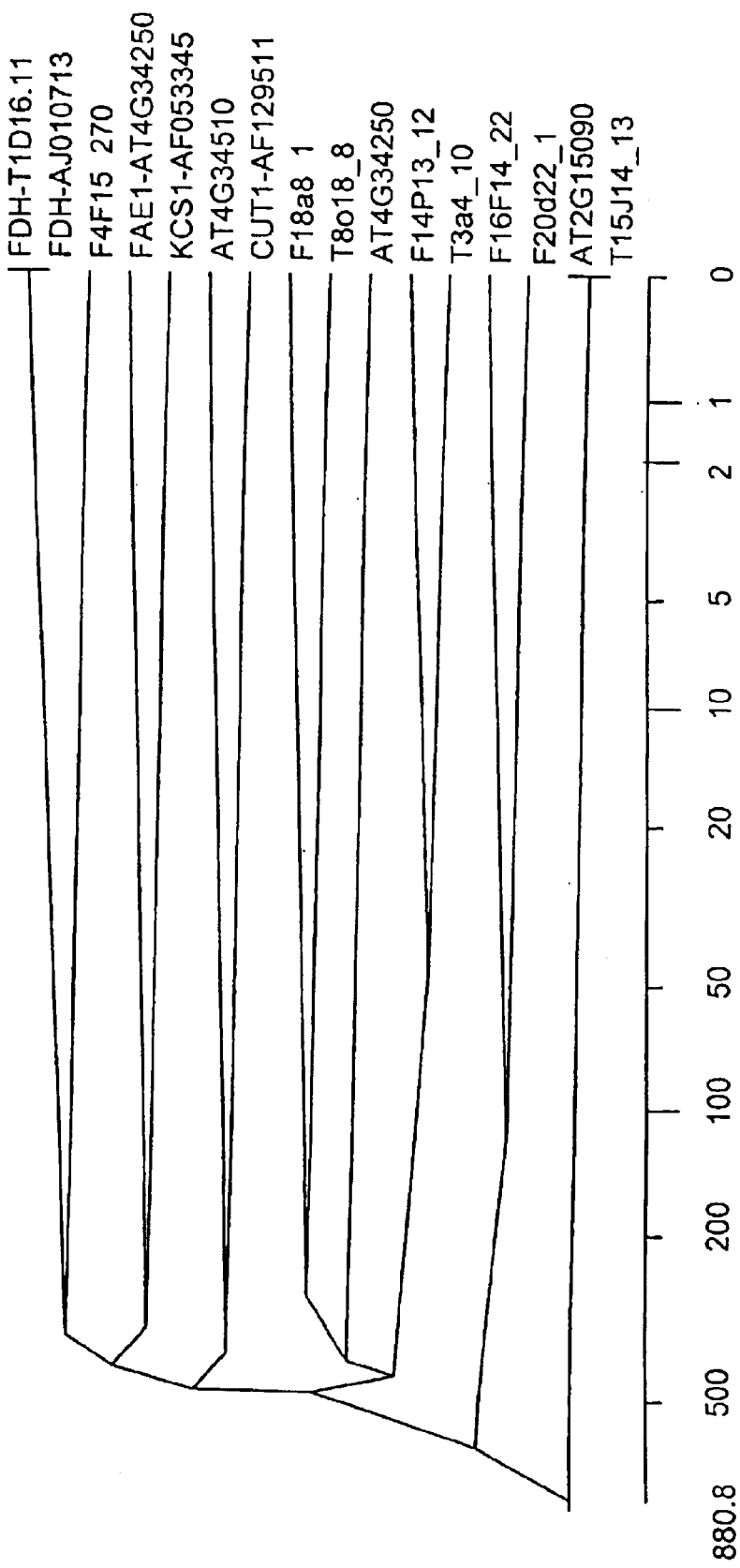

Symp. Soc. Exp. Biol. 11, (month unavailable) 1957, pp. 118–131, F. Skoog et al, "Chemical Regeneration of Growth and Organ Formation in Plant Tissue Cultures in Vitro".

"Inhibition of Very–Long–Chain Fatty Acid Biosynthesis by 2–Chloro–N–)3–methoxy–2–thenyl)–2',6'–dimethylacetanilide, Thenylchlor, and Its Analogs".

The Plant Cell, vol. 12, May, 2000, pp. 721–737, P. Sieber et al, "Transgenic Arabidopsis Plants Expressing a Fungal Cutinase Show Alterations in the Structure and Properties of the Cuticle and Postgenital Organ Fusions".

Schmalfuss Jochen et al: "Inhibition of acyl–CoA elongation by chloroacetamide herbicides in microsomes from leek seedlings." Pesticide Biochemistry and Physiology, Bd. 67, Nr. 1, Mai 2000 (May 2000), Seiten 25–35, XP001097160 ISSN: 0048–3575 Seite 27, rechhte Spalte, letzter Absatz–Seite 31, rechte Spalte, Absatz 1.

Abulnaja K O et al: "Inhibition of Fatty Acid Elongation Provides A Basis for the Action of the Herbicide Ethofumesate on Surface Wax Formation" Phytochemistry (Oxford), Bd. 31, Nr. 4, 1992, Seiten 1155–1159, XP008006655 ISSN: 0031–9422 Seite 1155, rechte Spalte, Absatz 1.

Bazoobandi M et al: "Analysis of flufenacet in soil, wheat grain and straw by gas chromatography" Journal of Chromatography, Elsevier Science Publishers B.V. Amsterdam, NL, Bd. 886, Nr. 1–2, Juli 2000 (Jul. 2000), Seiten 319–322, XP004205994 ISSN: 0021–9673 Seite 319, linke Spalte, Absatz 1.

Pesticide Biochemistry and Physiology, vol. 71, Issue 3, Nov. 2001, pp. 140–146 (See on line version pp. 1–7 attached), Hideomi Takahashi et al, Inhibition of Very–Long–Chain Fatty Acid Biosynthesis by 1–Chloro–N–(3–methoxy–2–thenyl)–2',6'–dimethylacetanilide, Thenylchlor, and Its Analogs.

* cited by examiner

USE OF VLCFAE FOR IDENTIFYING HERBICIDALLY ACTIVE COMPOUNDS

FIELD OF THE INVENTION

The invention relates to the use of nucleic acids which code for plant polypeptides with the biological activity of very long chain fatty acid elongases and to the use of the polypeptides encoded thereby for identifying novel, herbicidally active compounds, and to methods for finding modulators of these polypeptides.

BACKGROUND OF THE INVENTION

Fatty acid elongases are also referred to as 3-ketoacyl-CoA-synthases or as "condensing enzymes". Very long chain fatty acid elongases, abbreviated to VLCFAE hereinafter, are responsible for the biosynthesis of fatty acids with a chain length of more than 18 C atoms (Millar, A. A. and Kunst, L. 1997, The Plant Journal 12(1), 121–131). The substrates recognized by VLCFAE apart from malonyl-CoA ester are only fatty acid-CoA esters with chain lengths of greater than or equal to $C_{18}$ (C18+), and the proteins are probably microsomally associated in the cytoplasm. Synthesis of fatty acids with up to 18 C atoms de novo in plants takes place in the chloroplast, and the fatty acids are esterified by an acyl carrier protein (ACP), (WO 98/54954). Long-Chain Fatty Acids, referred to as VLCFA hereinafter, are components and precursors of the wax layer in the cuticle of plants. They may be components and precursors of cell membranes or constituents of specific storage triacylglycerides. However, they may also be constituents or precursors of lipids with a signal function or with a second messenger function in the plant, such as, for example, the sphingolipids. (Millar, A. A. and Kunst, L. 1997, The Plant Journal 12(1), 121–131, Millar et al. 2000, Trends in Plant Science 5, 95–101).

DETAILED DESCRIPTION

Biochemical research (Matthes et al., Z. Naturforsch. 1998, 53c, 1004–1011, Abulnaja and Harwood, Phytochemistry 1991, 30(5), 1445–1447) has revealed that herbicidal substance classes such as, for example, chloroacetamides, oxyacetamides and thiocarbamates inhibit the synthesis of long-chain fatty acids. However, this research did not show whether this takes place by direct inhibition of or interaction with fatty acid elongase enzymes. It is equally unclear which of the many elongases which occur in plants are inhibited. Biochemical and cell biology research have further revealed that compounds such as BAS 13–338 inhibit C18:1 fatty acid elongation (Möller and Albrecht 1994, J. Plant Physiol. 144, 376–384). The elongases involved were also unknown in this research.

VLCFAE are plant-specific genes which, for example in Arabidopsis, represent a complex family of genes. One gene in this family, fiddlehead, is specifically expressed in the epidermis, the outermost plant cell layer, and suppresses the dedifferentiation of these cells. Mutants in which the function of the FIDDLEHEAD-protein is impaired show fusions/adhesions of leaves and flower organs. The fusions/adhesions of the flower organs of a fiddlehead mutant resemble the scroll of a violin and gave this name to the mutant. Fiddlehead plants show considerable morphological changes and great impairments of development. (Lolle et al. 1992, Developmental Biology 152, 383–392, Yephremov et al. 1999, The Plant Cell 11, 2187–2201, Pruitt et al. 2000, PNAS 97(3), 1311–1316). Epidermal cells are essentially involved in the fusion/adhesion. Moreover the cells fuse only via the extracellular layer, without fusion of the cytoplasm. Since epidermal cells are responsible for the formation of the extracellular cuticle, it must be assumed that the loss of function of fiddlehead leads to a change in the VLCFA components in the cuticle and this causes the organ fusions described.

The nucleic acid coding for the FIDDLEHEAD polypeptide is available under the accession number AJ010713 or O64846 (GenEMBL) and is shown in WO 98/54954 and described in the present application under SEQ ID NO: 1.

The diversity of the elongases, their substrate specificity and their tissue-specific expression makes it possible for plants to produce a wide variety of storage, cuticle and signal lipids. This synthetic diversity can be utilized in practice through heterologous gene expression in transgenic plants. It is moreover possible by gene transfer for the synthetic capacity due to an elongase with specific substrate specificity to be transferred from one plant species to another. On the other hand, it is also possible, for example by exchange of promoters, for the tissue-specific lipid synthesis to be deliberately changed within one plant species. Diverse publications deal with research of this type. (see, for example, WO 96/13582, WO 98/46766, WO 98/54954, WO 95/15387, WO 00/08172).

It has now been found, surprisingly, that the fiddlehead phenotype can be induced with a herbicidal active substance from the oxyacetamide class, flufenacet. The active substance phenocopies fiddlehead. In addition, the active substance also leads to fusion of the rosette leaves.

The finding that the oxyacetamide flufenacet induces fiddlehead-like fusion of flower organs leads to the conclusion that FIDDLEHEAD (FDH), a very long chain fatty acid elongase, is the interaction partner (the target) of the herbicidal active substance.

Since the VLCFAE, in particular also FIDDLEHEAD from Arabidopsis and other plants, show extensive homologies with one another, it is also possible to use homologous polypeptides encoded by appropriate homologous nucleic acids, and other members of the gene family, as molecular interaction partners (targets) for herbicidal active substances and the aforementioned class of substances. It is thus possible for herbicidal active substances to interact with various VLCFAE, although the interaction with the various VLCFAE occurring in plants may not always have the same strength. This might explain inter alia the observed selectivity of the herbicide class. Other members of the gene family, such as fatty acid elongases and beta-ketoacyl-CoA synthases from Arabidopsis, which are homologous with FIDDLEHEAD (FDH) from *Arabidopsis thaliana* (Acc. No. AJ010713 or O64846) are listed by way of example and not definitively in the following table and in FIG. 1. The degree of phylogenetic relationship between the genes shown can also be inferred qualitatively therefrom.

| | Gene (Arabidopsis thaliana) | Accession Number | Description |
|---|---|---|---|
| 1 | T1D16.11 | tremb1\|AC004484\|AC004484_11 | putative beta-ketoacyl-CoA synthase |
| 2 | F18A8.1 | tremb1\|AC003105\|AC003105_1 | putative beta-ketoacyl-CoA synthase |
| 3 | F16F14.22 | tremb1\|AC007047\|AC007047_19 | putative beta-ketoacyl-CoA synthase |
| 4 | F20D22.1 | tremb1\|AC002411\|AC002411_1 | putative 3-oxoacyl-[acyl-carrier-protein] synthase (EC 2.3.1.41) |
| 5 | CUT1 | tremb1\|AF129511\|AF129511_1 | "very-long-chain fatty acid condensing enzyme" (CUT1) |
| 6 | KCS1 | tremb1\|AF053345\|AF053345_1 | fatty acid elongase 3-ketoacyl-CoA-synthase 1-gene ("KCS1"); KCS1-Product: "fatty acid elongase 3-ketoacyl-CoA synthase 1". |
| 7 | AT4g34510 | tremb1new\|AL161585\|ATCHRIV81_35 | putative ketoacyl-CoA synthase |
| 8 | T3A4.10 | tremb1\|AC005819\|AC005819_10 | putative beta-ketoacyl-CoA synthase |
| 9 | AT4g34250 | tremb1new\|AL161585\|ATCHRIV81_9 | fatty acid elongase-like protein |
| 10 | AT4g34520 (FAE 1) | tremb1new\|AL161585\|ATCHRIV81_36 | fatty acid elongase 1 (FAE 1) |
| 11 | F14P13.12 | tremb1\|AC009400\|AC009400_12 | putative fatty acid elongase 3-ketoacyl-CoA synthase 1 |
| 12 | F4F15.270 | tremb1\|AL049711\|ATF4F1S_27 | beta-ketoacyl-CoA synthase-like protein |
| 13 | T8O18.8 | tremb1\|AC007171\|AC007171_8 | putative fatty acid elongase |

A conclusion in the publication by Böger et al. 2000 (Pest Manag. Sci. 56, 497–508) is that plant VLCFAE are the primary targets of chloroacetamides.

However, it is found in the present application for the first time by the example of the FIDDLEHEAD VLCFAE that VLCFAE are protein targets for herbicidal active substances and can be employed to identify novel, improved herbicidal active substances in methods (assays) suitable for this purpose.

This applies in particular to polypeptides from plants showing a homology to the FIDDLEHEAD (FDH) polypeptide from Arabidopsis, preferably encompassing polypeptides with a homology of 60%, particularly preferably of 80% and very particularly preferably of 90%, to FDH.

Particular preference is given in this connection to FDH-homologous VLCFAE from Arabidopsis for identifying novel, herbicidal active substances, preferably encompassing polypeptides with a homology of 60%, particularly preferably of 80% and very particularly preferably of 90%, to FDH.

It is possible in a very particularly preferred manner for the FDH polypeptide from Arabidopsis to be used to identify novel herbicidal active substances.

The present invention therefore relates to the use of plant polypeptides with the biological activity of a VLCFAE for identifying VLCFAE modulators.

The present invention likewise relates to the use of plant polypeptides with the biological activity of a VLCFAE having a homology of 60%, preferably of 80% and particularly preferably of 90% to the FDH polypeptide from Arabidopsis for identifying VLCFAE modulators.

The present invention likewise relates to the use of polypeptides from Arabidopsis with the biological activity of a VLCFAE which have a homology of 60%, preferably of 80% and particularly preferably of 90% to the FDH polypeptide from Arabidopsis for identifying VLCFAE modulators.

The present invention relates in particular to the use of the FIDDLEHEAD polypeptide having SEQ ID NO: 2 for identifying VLCFAE modulators.

The present invention likewise relates to the use of nucleic acids encoding for VLCFAE for identifying VLCFAE modulators.

The present invention likewise relates to the use of nucleic acids coding for VLCFAE and having a homology to the fiddlehead sequence according to a coding sequence of SEQ ID NO: 1 of 60%, preferably of 80% and particularly preferably of 90% for identifying VLCFAE modulators. Homologues of Arabidopsis are particularly preferred in this connection.

The present invention relates in particular also to the use of the nucleic acid coding for the FIDDLEHEAD polypeptide and having SEQ ID NO: 1 for identifying VLCFAE modulators.

The polynucleotides or polynucleotide fragments to be used according to the invention are preferably those corresponding to polynucleotides from plants.

The polynucleotides or polynucleotide fragments to be used according to the invention are particularly preferably those corresponding to polynucleotides from Arabidopsis.

The polypeptides to be used according to the invention very particularly preferably include a sequence selected from
  a) the sequence shown in SEQ ID NO: 2,
  b) sequences encoded by a nucleic acid having SEQ ID NO: 1,
  c) partial sequences of the sequences defined under a) or b) which still have the biological activity of a VLCFAE,
  d) sequences which have an identity of at least 60%, preferably of 80%, particularly preferably of 90%, with the sequences defined under a) to c),
  e) sequences which include the C-terminally localized active site of the polypeptide shown in SEQ ID NO: 2,
  f) sequences which have an identity of at least 60%, preferably of 80%, particularly preferably of 90%, with the sequences defined under e),
  g) sequences which include the specific N terminus of the polypeptide shown in SEQ ID NO: 2, and
  h) sequences which have an identity of at least 60%, preferably of 80%, particularly preferably of 90%, with the sequences defined under g).

A very particularly preferred embodiment of the nucleic acids to be used according to the invention is represented by a cDNA molecule having the FDH-encoding sequence shown in SEQ ID NO: 1, the introns shown in SEQ ID NO: 1 no longer being present.

The FDH-encoding regions of the nucleic acid shown in SEQ ID NO: 1 extend from position 176–583, 1119–1745 and 1821–2438.

The nucleic acids to be used according to the invention are, in particular, single-stranded or double-stranded deoxyribonucleic acids (DNA) or ribonucleic acids (RNA). Preferred embodiments are fragments of genomic DNA, which may contain introns as shown in SEQ ID NO: 1 and cDNAs.

The nucleic acids to be used according to the invention are preferably DNA or DNA fragments corresponding to genomic DNA from plants.

The nucleic acids to be used according to the invention are particularly preferably DNA or DNA fragments corresponding to genomic DNA from Arabidopsis.

The nucleic acids to be used according to the invention very particularly preferably include a sequence selected from a) the sequence shown in SEQ ID NO: 1, b) sequences which code for a polypeptide including the amino acid sequence shown in SEQ ID NO: 2, c) partial sequences at least 14 base-pairs long of the sequences defined under a) or b), d) sequences which hybridize to the sequences defined under a) or b), e) sequences which have an identity of at least 60%, preferably of 80%, particularly preferably of 90%, with the sequences defined under a) or b), f) sequences which code for the C-terminally localized active site of the polypeptide shown in SEQ ID NO: 2 g) sequences which have an identity of at least 60%, preferably of 80%, particularly preferably of 90%, with the sequences defined under f), h) sequences which code for the specific N terminus of the polypeptide shown in SEQ ID NO: 2, i) sequences which have an identity of at least 60%, preferably of 80%, particularly preferably of 90%, with the sequences defined under h), j) sequences which are complementary to the sequences defined under a) to i), and k) sequences which, because of the degeneracy of the genetic code, code for the same amino acid sequence as the sequences defined under a) to h).

A very particularly preferred embodiment of the nucleic acids to be used according to the invention is represented by a cDNA molecule with the FDH-encoding sequence shown in SEQ ID NO: 1.

The term "to hybridize" as used herein describes the process in which a single-stranded nucleic acid molecule enters into base pairing with a complementary strand. It is possible in this way, starting from the sequence information disclosed herein, for example to isolate DNA fragments from plants other than Arabidopsis which code for VLCFAE and, in particular, for FIDDLEHEAD, which have the same or similar properties of an elongase with the amino acid sequence shown in SEQ ID NO: 2. Thus, for example, the nucleic acid sequence coding for the N-terminal polypeptide sequence characteristic of FDH can be used in order to find nucleic acid sequences and polypeptides which are sequentially and functionally homologous to FDH and are suitable for identifying novel herbicidal active substances.

Hybridization conditions are calculated approximately by the following formula:

The melting temperature $Tm=81.5°\ C.+16.6\ \log[c(Na^+)]+0.41(\%\ G+C)-500/n$ (Lottspeich and Zorbas, 1998).

In this, c is the concentration and n is the length of the hybridizing sequence section in basepairs. The term 500/n is omitted for a sequence of >100 bp. With the highest stringency, washing is carried out at a temperature of 5–15° C. below Tm and an ionic strength of 15 mM Na+ (equivalent to 0.1×SSC). If an RNA probe is used for the hybridization, then the melting point is 10–15° C. higher.

Preferred hybridization conditions are indicated below:

Hybridization solution: DIG Easy Hyb (supplied by Roche) Hybridization temperature: 37° C., preferably 42° C. (DNA—DNA), 50° C. (DNA-RNA).

1. washing step: 2x SSC, 0.1% SDS 2×5 min at room temperature;

2. washing step: 1x SSC, 0.1% SDS 2x 15 min at 50° C.; preferably 0.5x SSC, 0.1% SDS 2x 15 min at 65° C.; particularly preferably 0.2x SSC, 2×15 min at 68° C.

The term "active site" refers to a peptide region which functionally corresponds to the peptide region with an amino acid sequence from position 191 to position 310 of the sequence shown in SEQ ID NO: 2. The reactive amino acid cystein is located at position 257.

The degree of identity of the nucleic acids is preferably determined with the aid of the NCBI BLASTN program, version 2.0.4. (Altschul et al., 1997).

The present invention also relates to the use, in methods for identifying VLCFAE inhibitors, of the regulatory regions which, in plant cells, especially in Arabidopsis, naturally control the transcription of the nucleic acids to be used according to the invention.

The term "regulatory regions" as used herein refers to nontranslated regions of the relevant gene, such as promoters, enhancers, repressor or activator binding sites or termination sequences, which interact with cellular proteins, leading to control of transcription.

The present invention further relates to the use of DNA constructs which include a nucleic acid to be used according to the invention and a heterologous promoter for identifying VLCFAE modulators.

The term "heterologous promoter" as used herein refers to a promoter which has properties different from those of the promoter which controls expression of the relevant gene in the original organism.

The selection of heterologous promoters depends on whether prokaryotic or eukaryotic cells or cell-free systems are used for expression. Examples of heterologous promoters are the 35S promoter of cauliflower mosaic virus for plant cells, the alcohol dehydrogenase promoter for yeast cells, the T3, T7 or SP6 promoters for prokaryotic cells or cell-free systems, and tissue-specific promoters from plants, for example the epidermis-specific promoter of FIDDLEHEAD and the promoters of other tissue-specific elongases.

The present invention further relates to the use of vectors which contain a nucleic acid to be used according to the invention, a regulatory region to be used according to the invention or a DNA construct to be used according to the invention, in methods for identifying the VLCFAE modulators.

Vectors which can be used are all phages, plasmids, phagemids, phasmids, cosmids, YACs, BACs, artificial chromosomes or particles suitable for particle bombardment which are used in molecular biology laboratories.

Preferred vectors are pBIN (Bevan, 1984) and its derivatives for plant cells, pFL61 (Minet et al., 1992) or, for example, the p4XXprom vector series (Mumberg D., Müller R. and Funk M. 1995, Gene 156, 119–122) for yeast cells, pBLUESCRIPT-vectors for bacterial cells, lamdaZAP (from Stratagene) for phages.

The present invention also relates to the use of host cells which contain a nucleic acid to be used according to the invention, a DNA construct to be used according to the invention or a vector to be used according to the invention, for identifying VLCFAE modulators.

The term "host cell" as used herein refers to cells which do not naturally contain the nucleic acids to be used according to the invention and are suitable for expression of the polypeptide to be used according to the invention.

Suitable host cells are both prokaryotic cells, preferably *E. coli*, and eukaryotic cells such as cells of *Saccharomyces cerevisiae, Pichia pastoris*, insects, plants, frog oocytes and mammalian cell lines.

The term "polypeptides" as used herein refers both to short amino acid chains, which are usually referred to as peptides, oligopeptides or oligomers, and to longer amino acid chains which are usually referred to as proteins. It encompasses amino acid chains which may be modified either by natural processes, such as post-translational processing, or by chemical methods which are state of the art. Such modifications may occur at various points and a plurality of times in a polypeptide, such as, for example, on the peptide backbone, on the amino acid side chain, on the amino terminus and/or on the carboxyl terminus. They comprise, for example, acetylations, acylations, ADP ribosylations, amidations, covalent linkages with flavins, haem portions, nucleotides or nucleotide derivatives, lipids or lipid derivatives or phosphatidylinositol, cyclizations, formation of disulphide bridges, demethylations, cystine formations, formylations, gamma-carboxylations, glycosylations, hydroxylations, iodinations, methylations, myristoylations, oxidations, proteolytic processings, phosphorylations, selenoylations and tRNA-mediated additions of amino acids.

The peptides according to the invention may be in the form of "mature" proteins or in the form of parts of larger proteins, for example as fusion proteins. They may furthermore have secretion or "leader" sequences, prosequences, sequences which make simple purification possible, such as multiple histidine residues, or additional stabilizing amino acids.

The polypeptides to be used according to the invention need not be complete VLCFAE but may also be only fragments thereof as long as they still have a biological activity of the complete VLCFAE. Polypeptides which exercise a biological activity of the same type as a VLCFAE with an amino acid sequence as shown in SEQ ID NO: 2 are also regarded as being according to the invention. The polypeptides to be used according to the invention moreover need not correspond to the VLCFAE from Arabidopsis. Also regarded as polypeptides to be used according to the invention are polypeptides which are homologous to VLCFAE for example of the following plants or to fragments thereof which can still exercise the biological activity of the latter:

Dicotyledonous plants of the genera: Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.

Dicotyledonous plants of the genera: Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Vicia.

Monocotyledonous plants of the genera: Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.

Monocotyledonous plants of the genera: Allium, Ananas, Asparagus, Avena, Hordeum, Oryza, Panicum, Saccharum, Secale, Triticale, Triticum, Zea.

The polypeptides to be used according to the invention may, by comparison with the corresponding region of naturally occurring VLCFAE, have deletions or amino acid substitutions as long as they still exercise the biological activity of the complete fatty acid elongases. Conservative substitutions are preferred. Such conservative substitutions comprise variations where one amino acid is replaced by another amino acid from the following group:

1. small aliphatic residues which are nonpolar or of low polarity: Ala, Ser, Thr, Pro and Gly;
2. polar, negatively charged residues and their amides: Asp, Asn, Glu und Gln;
3. polar, positively charged residues: His, Arg and Lys;
4. large aliphatic, nonpolar residues: Met, Leu, Ile, Val and Cys; and
5. aromatic residues: Phe, Tyr und Trp.

The following list shows preferred conservative substitutions:

| Original residue | Substitution |
| --- | --- |
| Ala | Gly, Ser |
| Arg | Lys |
| Asn | Gln, His |
| Asp | Glu |
| Cys | Ser |
| Gln | Asn |
| Glu | Asp |
| Gly | Ala, Pro |
| His | Asn, Gln |
| Ile | Leu, Val |
| Leu | Ile, Val |
| Lys | Arg |
| Met | Leu, Tyr, Ile, Phe |
| Phe | Met, Leu, Tyr, Trp |
| Ser | Thr |
| Thr | Ser |
| Trp | Tyr, Phe |
| Tyr | Trp, Phe |
| Val | Ile, Leu |

The present invention thus also relates to the use of polypeptides which exercise the biological activity of a VLCFAE and comprise an amino acid sequence which shows at least 60% identity, preferably 80% identity, particularly preferably 90% identity and particularly preferably 97–99% identity with the sequence shown in SEQ ID NO: 2 over the entire length thereof.

The degree of identity of the amino acid sequences is preferably determined with the aid of the BLASTP+ BEAUTY programme, version 2.0 4. (Altschul et al., 1997).

A preferred embodiment of the polypeptides to be used according to the invention is the VLCFAE FIDDLEHEAD (FDH) with an amino acid sequence as shown in SEQIDNO: 2.

The FDH amino acid sequence belongs on the basis of homology (Yephremov et al. 1999) to the family of fatty acid elongases (FAE). The FDH protein has two potential transmembranes domains in the region of the amino acids from about 53 to 75 and in the region from about 93 to 115.

The first 45–50 amino acids at the N terminus are specific for the FIDDLEHEAD protein whose biological role has not as yet been fully elucidated. The N terminus is so specific that it can be used as recognition sequence for FDH.

The term "biological activity of a VLCFAE" as used herein means the ability to biosynthesize fatty acids with a chain length of 18 and more C atoms, and to the recognition of the substrates malonyl-CoA esters and/or fatty acid CoA esters with chain lengths greater than or equal to $C_{18}$.

The nucleic acids to be used according to the invention can be prepared in the conventional way. For example, the nucleic acid molecules can be completely chemically synthesized. It is also possible for short pieces of the nucleic acids according to the invention to be chemically synthesized and for such oligonucleotides to be labelled radioactively or with a fluorescent dye. The labelled oligonucleotides can also be used to screen cDNA banks produced starting from plant mRNA. Clones to which the labelled oligonucleotides hybridize are selected for isolating the relevant DNA fragments. After characterization of the isolated DNA, the nucleic acids to be used according to the invention are obtained in a simple manner.

The nucleic acids to be used according to the invention can also be prepared by PCR methods using chemically synthesized oligonucleotides.

The term "oligonucleotide(s)" as used herein means DNA molecules consisting of 10 to 50 nucleotides, preferably 15 to 30 nucleotides. They are chemically synthesized and can be used as probes.

The polypeptides to be used according to the invention which are encoded by the nucleic acids according to the invention can be prepared by cultivating, under suitable conditions, host cells which contain nucleic acids to be used according to the invention. The desired polypeptides can then be isolated in a conventional way from the cells or the culture medium. The polypeptides can also be prepared in in-vitro systems.

A rapid method for isolating the polypeptides to be used according to the invention which are synthesized by host cells using a nucleic acid to be used according to the invention starts with the expression of a fusion protein where the fusion partner can be affinity-purified in a simple manner. The fusion partner can be, for example, glutathione S-transferase. The fusion protein can then be purified on a glutathione affinity column. The fusion partner can be removed by partial proteolytic cleavage for example at linkers between the fusion partner and the polypeptide according to the invention which is to be purified. The linker can be designed so that it includes target amino acids, such as arginine and lysine residues, which define sites for trypsin cleavage. Such linkers can be generated by employing standard cloning methods using oligonucleotides.

Further possible purification methods are based on preparative electrophoresis, FPLC, HPLC (for example using gel filtration, reverse phase or slightly hydrophobic columns), gel filtration, differential precipitation, ion exchange chromatography and affinity chromatography.

Since VLCFAE are membrane proteins or membrane-associated proteins, detergent extractions are preferably carried out during the purification methods, for example using detergents which affect the secondary and tertiary structures of the polypeptides only slightly or not at all, such as nonionic detergents.

Purification of the polypeptides to be used according to the invention may encompass the isolation of membranes starting from host cells which express the nucleic acids according to the invention. Such cells preferably express the polypeptides to be used according to the invention in an adequate copy number so that the amount of polypeptides in a membrane fraction is at least 10 times higher than that found in comparable membranes of cells which express the FDH gene naturally; the amount is particularly preferably 100 times, very particularly preferably at least 1000 times, higher.

For assay purposes it is also possible for a membrane fraction, in particular a microsome fraction, to be concentrated and used without special purification.

The terms "isolation or purification" as used herein mean that the polypeptides to be used according to the invention are separated from other proteins or other macromolecules of the cell or of the tissue. A composition containing the polypeptides to be used according to the invention is preferably concentrated at least 10-fold and particularly preferably at least 100-fold in terms of the protein content by comparison with a preparation from the host cells.

The polypeptides to be used according to the invention can be affinity-purified even without fusion partners, with the aid of antibodies which bind to the polypeptides.

The present invention also relates to methods for finding chemical compounds which bind to the polypeptides according to the invention and alter their properties. Because of the diverse functions of the VLCFAE according to the invention, modulators which influence the activity may represent novel growth-regulating or herbicidal active substances. Modulators may be agonists or antagonists, or inhibitors or activators.

The term "agonist" as used herein refers to a molecule which promotes or enhances the VLCFAE activity.

The term "antagonist" as used herein refers to a molecule which retards or impedes the VLCFAE activity.

The term "modulator" as used herein represents the generic term for agonist and antagonist. Modulators may be small organic chemical molecules, peptides or antibodies which bind to the polypeptides according to the invention. Modulators may furthermore be small organic chemical molecules, peptides or antibodies which bind to a molecule which in turn binds to the polypeptides according to the invention and thus influences their biological activity. Modulators may be natural substrates and ligands or structural or functional mimetics thereof.

The modulators are preferably small organic chemical compounds.

Binding of the modulators to the VLCFAE may alter the cellular processes in a way leading to death of the plants treated therewith.

The present invention therefore also relates to VLCFAE modulators which have been found with the aid of a method described above for identifying modulators of the FDH protein or of a VLCFAE homologous thereto.

The present invention further relates to methods for finding chemical compounds which alter the expression of the polypeptides to be used according to the invention. Such "expression modulators" may also represent novel growth-regulating or herbicidal active substances. Expression modulators may be small organic chemical molecules, peptides or antibodies which bind to the regulatory regions of the nucleic acids coding for the polypeptides to be used according to the invention. Expression modulators may furthermore be small organic chemical molecules, peptides or antibodies which bind to a molecule which in turn binds to regulatory regions of the nucleic acids coding for the polypeptides to be used according to the invention, and thus influences expression thereof. Expression modulators may also be antisense molecules.

The present invention likewise relates to the use of modulators of the polypeptides to be used according to the invention or of expression modulators as plant growth regulators or herbicides.

The present invention likewise relates to expression modulators of VLCFAE which are found with the aid of the method described above for finding expression modulators.

The methods according to the invention include high-throughput screening (HTS). It is possible to use for this both host cells and cell-free preparations which contain the nucleic acids to be used according to the invention and/or the polypeptides to be used according to the invention.

In order to find modulators it is possible to incubate a synthetic reaction mix (for example products of in vitro transcription) or a cellular constituent, such as a membrane or any other preparation which contains the polypeptides to be used according to the invention, together with a labelled substrate or ligand of the polypeptides in the presence and absence of a candidate molecule which may be an agonist or antagonist. The ability of the candidate molecule to increase or inhibit the activity of the polypeptides to be used according to the invention is evident from an increased or reduced binding of the labelled ligand or from an increased or reduced conversion of the labelled substrate. Molecules which bind well and lead to an increased activity of the polypeptides according to the invention are agonists. Molecules which bind well and inhibit the biological activity of the polypeptides to be used according to the invention are good antagonists. These may be inhibitors of the abovementioned classes of herbicidal substances without, however, being restricted thereto.

Detection of the biological activity of the polypeptides to be used according to the invention can be improved by a so-called reporter system. Reporter systems in this regard comprise, but are not restricted to, calorimetrically labelled substrates which are converted into a product, or a reporter gene which responds to changes in the activity or the expression of the polypeptides to be used according to the invention, or other known binding assays.

The activity of membrane-associated proteins can advantageously be measured in another way. Functional heterologous expression of such proteins in *E. coli* is often difficult or impossible. In this case it is possible by suitable cloning (for example using suitable PCR strategies) to separate the catalytically active part of the protein from the membrane-associated part of the protein so that the gene product represents a soluble protein and can easily be purified. A wide repertoire of measurement possibilities is available for measuring the activity of soluble proteins. Particularly sensitive measurement can take place for example by fluorescence polarization with use of a fluorescence-labelled ligand or substrate.

Another example of a method with which modulators of the polypeptides to be used according to the invention can be found is a displacement assay in which, under conditions suitable for this purpose, the polypeptides to be used according to the invention and a potential modulator are compacted with a molecule which is known to bind to the polypeptides to be used according to the invention, such as a natural substrate or ligand or a substrate or ligand mimetic. The substrate or ligand mimetic may be, for example, radioactively labelled or provided with a fluorescent or dye marker (also UV). The polypeptides to be used according to the invention themselves can also be labelled in an analogous way so that the number of polypeptides which are bound to a ligand or have undergone a reaction can be determined accurately. It is possible in this way to estimate the efficacy of an agonist or antagonist.

The invention further relates to the use of a nucleic acid to be used according to the invention, of a DNA construct to be used according to the invention or of a vector to be used according to the invention for producing transgenic plants, and to the corresponding transgenic plants as such or parts or propagation material thereof.

The present invention likewise relates to transgenic plants, parts of plants, protoplasts, plant tissues or plant propagation materials in which, after introduction of a nucleic acid to be used according to the invention, of a DNA construct to be used according to the invention or of a vector to be used according to the invention, the intracellular concentration of VLCFAE is increased or reduced compared with the corresponding wild-type forms.

The term "parts of plants" as used herein means all epigeal and hypogeal parts and organs of the plants, such as shoot, leaf, flower and root, and protoplasts and tissue cultures produced therefrom.

The term "propagation material" as used herein means vegetative and generative propagation material such as cuttings, tubers, rhizomes, layers and seeds.

The invention also relates to plants in which alterations are made in the sequence coding for VLCFAE leading to production of a VLCFAE which leads to an increase or reduction in the biological activity or the amount of the VLCFAE present in the plants.

The term "mutagenesis" as used herein refers to a method for increasing the spontaneous mutation rate and thus for isolating mutants. This may entail generation of mutants with the aid of mutagens in vivo, for example with chemical compounds or physical effects which are suitable for inducing mutations (for example base analogues, intercalating substances, UV rays etc.). The required mutants can be obtained by selection for a particular phenotype. The position of the mutations on the chromosomes can be determined relative to other known mutations by complementation and recombination analyses. Mutations can also be introduced in a targeted manner into chromosomal or extrachromosomal DNA (in vitro mutagenesis, site directed mutagenesis, error-prone PCR etc.).

The term "mutant" as used herein refers to an organism which harbours an altered (mutated) gene. A mutant is defined by comparison with the wild-type which harbours the unaltered gene.

Since the VLCFAE to be used according to the invention, in particular the FDH protein, plays a part in signalling and development processes, transgenic "sense" plants or plants which have been selected deliberately for an increased amount or activity of corresponding endogenous VLCFAE or elements linked thereto in the signal transduction acquire increased resistance to herbicidally active compounds. It is also possible by mutating the amino acid sequence to develop VLCFAE which are resistant to compounds having herbicidal activity on these proteins. Transfer and expression of the genes of such naturally isolated or synthetically produced mutants in plants, especially in crop plants such as, for example, maize, wheat, barley, oats, rice, rye, tomatoes, legumes, potato plants, Lactuca sativa, Brassicaceae, wood plants, Physcomitrella patens, makes them herbicide-resistant or characterized by increased tolerance to herbicides.

EXAMPLES

Example 1
Herbicide Treatment of *Arabidopsis thaliana* With Flufenacet: Generation of the Fiddlehead Phenotype Arabidopsis seeds (ecotype Columbia Col-0), which were stored at 4° C., were sown in soil and cultivated at 22° C.±2° C. under long-day conditions (16 h light/8h dark).

Plants 2 weeks old were sprayed with 250 g/ha and 50 g/ha flufenacet and cultivated further at 22° C.±2° C. under long-day conditions (16 h light/8h dark). Between day 7 and day 11 after flufenacet treatment, the flower organs fuse with the uppermost cauline leaves of the Arabidopsis plants. These fusions are very similar to those in the "fiddlehead" mutants. From day 18, all the flowers appear normal again because flufenacet is degraded by the glutathione S-transferase activity of the plants.

Example 2
Isolation of the Described FDH Nucleotide Sequence

Isolation of the described FIDDLEHEAD (FDH) nucleotide sequence can take place in analogy to Yephremov et al. 1999, The Plant Cell 11, 2187–2201, Pruitt et al. 2000, PNAS 97(3), 1311–1316 or as described in WO 98/54954 (clone EL 4). The sequence can also be obtained straightforwardly by methods known to the skilled person with the assistance of the sequence described in SEQ ID NO: 1.

Example 3
Production of Transgenic Arabidopsis Plants Resistant to Active Substances Directed Against VLCFAE Selected, mutated VLCFAE gene constructs are cloned into suitable pBIN vector constructs and transferred to suitable agrobacteria strains. The vector sequences harbour a marker gene which can be selected in plants and which confers, for example, resistance to kanamycin or resistance to the herbicide BASTA. Arabidopsis plants are grown and, after 4–6 weeks, shortly before flowering, immersed in a suspension of the agrobacteria strain transformed with the vector construct. Contact of the plant tissue with the bacteria suspension can be enhanced by vacuum infiltration. The plants treated in this way are incubated further until the seeds are ripe. The seeds are harvested and placed on selection medium. The only seedlings to survive are those containing the transferred gene construct and the marker gene, those which have thus been successfully transformed. A detailed description of the method can be found in Bechthold N. and Pelletier G.: *In planta Agrobacterium* mediated transformation of adult *Arabidopsis thaliana* plants by vacuum infiltration. In: Arabidopsis Protocols, edited by Martinez-Zapater J. M. and Salinas J., 1998 Humana Press ISBN 0-89603-391-0.

Explanation of the Figures and of the Sequence Listing

FIG. 1: Phylogenetic tree of *Arabidopsis thaliana* beta-ketoacyl-CoA synthases with homology to FIDDLEHEAD (FDH) (DNA Star Program MegAlign (Clustal method with PAM250 "residue weight table")).

SEQ ID NO: 1: Nucleic acid sequence coding for the "FIDDLEHEAD" (FDH) polypeptide from *Arabidopsis thaliana*, a very long chain fatty acid elongase. This is a genomic sequence, which is why introns are still present. The coding regions are indicated.

SEQ ID NO: 2: Amino acid sequence of the "FIDDLEHEAD" (FDH) polypeptide from *Arabidopsis thaliana*.

REFERENCES

Abulnaja K.O. and Harwood J.L. 1991, Thiocarbamate Herbicides inhibit fatty acid elongation in a variety of monocotyledons. Phytochemistry 30(5), 1445–1447).

Altschul S.F., Madden T.L., Schaffer A.A., Zhang J.Z.; Miller W. and Lipman, D.J. 1997. Gapped BLAST and PSI-BLAST generation of protein database search programs. Nucleic Acids Res. 25: 3389–3402.

Bechthold N. mid Pelletier G. In *planta Agrobacterium* mediated transformation of adult *Arabidopsis thaliana* Plants by vacuum infiltration. In: Arabidopsis Protocols, edited by Martinez-Zapater J.M. und Salinas J., 1998 Humana Press ISBN 0-89603-391-0.

Bevan, M., Binary Agrobacterium vectors for plant transformation (1984), Nucl. Acids Res. 12 (22), 8711–8721.

Böger P., Matthes B. und Schmalfuβ J. 2000, Towards the primary target of chloroacetamides—new findings pave the way. Pest Management Science 56: 497–508.

Lottspeich, F., Zorbas H. (editors). 1998. Bioanalytik. Spektrum Akademischer Verlag, Heidelberg, Berlin.

Matthes B., Schmalfuβ J. and Boeger P. 1998, Chloracetamide Mode of Action II: Inhibition of Very Long Chain Fatty Acid Synthesis in Higher Plants. Z. Naturforsch. 53c, 1004–1011.

Millar A.A. and Kunst L. 1997, Very-long-chain fatty acid biosynthesis is controlled through the expression and specificity of the condensing enzyme. The Plant Journal 12(1), 121–131.

Millar A.A, Smith M.A., Kunst L. 2000, All fatty acids are not equal: discrimination in plant membrane lipids. Trends in Plant Science 5, 95–101.

Minet, M., Dufour, M.-E. and Lacroute, F. 1992. Complementation of *Saccharomyces cerevisiae* auxotrophic mutants by *Arabidopsis thaliana* cDNAs. Plant J. 2:417–422.

Möllers C. and Albrecht S. 1994, Screening herbicide effects on lipid metabolism of storage lipids by in vitro culture of microspore-derived embryoids of *Brassica napus*. J. Plant Physiol. 144, 376–384.

Mumberg D., Müller R. and Funk M. 1995, Yeast vectors for the controlled expression of heterologous proteins in different genetic backgrounds. Gene 156, 119–122.

Pruitt R.E., Vielle-Calzada J-P., Ploense S.E., Grossniklaus U. and Lolle S.J. 2000, FIDDLEHEAD, a gene required to suppress epidermal cell interactions in Arabidopsis, encodes a putative lipid biosynthetic enzyme. PNAS 97(3), 1311–1316.

Puissant, C. and Houdebine, L.-M. 1990. An improvement of the single-step method of the RNA isolation by acid guanidinium thiocyanate-phenol-chloro form extraction. BioTechniques 8:148–149.

Skoog, F., Miller, C.O. 1957. Chemical regeneration of growth and organ formation in plant tissue cultures in vitro. Sytmp. Soc. Exp. Biol. 11: 118–131.

WO 2000/008172
WO 95/15387
WO 96/13 582
WO 98/46766
WO 98/54954

Yephremov A., Wismann E., Huijser P., Huijser C., WellesenK, Saedler H. 1999, Characterization of the FIDDLEHEAD Gene of Arabidopsis reveals a link between adhesion response and cell differentiation in the epidermis.The Plant Cell 11, 2187–2201.

What is claimed is:

1. A method for identifying herbicides, comprising the steps of contacting a polypeptide having the sequence of SEQ ID NO: 2 with a chemical compound or a mixture of chemical compounds under conditions which permit the interaction of the chemical compound or the mixture of chemical compounds with the polypeptide, and determining the chemical compound which specifically inhibits the enzymatic activity of the polypeptide.

2. A method of identifying herbicides, comprising the steps of contacting a polypeptide with the enzymatic activity of a very long chain fatty acid elongase and having an identity of at least 90% to the sequence of SEQ ID NO: 2 with a chemical compound or a mixture of chemical compound under conditions which permit the interaction of the chemical compound or the mixture of the chemical compounds with the polypeptide and determining the chemical compound which inhibits the enzymatic activity of the polypeptide.

3. A method for identifying herbicides, comprising the steps of contacting a host cell containing a nucleic acod coding for a polypeptide having the sequence of SEQ ID NO: 2 with a chemical compound or a mixture of chemical compounds under conditions which permit the interaction of the chemical compound or the mixture of chemical compounds with the polypeptide, and determining the chemical compound which specifically inhibits the enzymatic activity of the polypeptide.

4. A method for identifying herbicides, comprising the steps of contacting a host cell containing a polypeptide with the enzymatic activity of a very long chain fatty acid elongase and having an identity of at least 90% to the sequence of SEQ ID NO: 2 with a chemical compound or a mixture of chemical compounds under conditions which permit the interaction of the chemical compound or the mixture of chemical compounds with the polypeptide, and determining the chemical compound which specifically inhibits the enzymatic activity of the polypeptide.

5. A method according to claim 3, wherein the host cell is selected from the group consisting of *E. coil* cells, yeast cells, insect cells, mammalian cells and plant cells.

* * * * *

SEQUENCE LISTING

<160> NUMBER OF SEQ ID NOS: 2

<210> SEQ ID NO 1
<211> LENGTH: 2782
<212> TYPE: DNA
<213> ORGANISM: Arabidopsis thaliana
<220> FEATURE:
<221> NAME/KEY: CDS
<222> LOCATION: (176)..(583)
<221> NAME/KEY: CDS
<222> LOCATION: (1119)..(1745)
<221> NAME/KEY: CDS
<222> LOCATION: (1821)..(2438)

<400> SEQUENCE: 1

```
acattaacta cctctcacca accaccaaac ccaatcccca caatattacc attactctca      60
tataactaca catattcata tttacattt tgccaacac  aactccttat aagatataca     120
cttcatcaac ctatagatct cactcacata atcaacctac aaaacaaaaa caaga atg     178
                                                                Met
                                                                  1 ggt aga tcc aac gag caa gat ctg ctc tct acc gag atc gtt aat cgt      226
Gly Arg Ser Asn Glu Gln Asp Leu Leu Ser Thr Glu Ile Val Asn Arg
          5                  10                  15 ggg atc gaa cca tcc ggt cct aac gcc ggc tca cca acg ttc tcg gtt      274
Gly Ile Glu Pro Ser Gly Pro Asn Ala Gly Ser Pro Thr Phe Ser Val
     20                   25                  30 agg gtc agg aga cgt ttg cct gat ttt ctt cag tcg gtg aac ttg aag      322
Arg Val Arg Arg Arg Leu Pro Asp Phe Leu Gln Ser Val Asn Leu Lys
 35                  40                  45 tac gtg aaa ctt ggt tac cac tac ctc ata aac cat gcg gtt tat ttg      370
Tyr Val Lys Leu Gly Tyr His Tyr Leu Ile Asn His Ala Val Tyr Leu
 50                  55                  60                  65 gcg acc ata ccg gtt ctt gtg ctg gtt ttt agt gct gag gtt ggg agt      418
Ala Thr Ile Pro Val Leu Val Leu Val Phe Ser Ala Glu Val Gly Ser
                 70                  75                  80 tta agc aga gaa gag att tgg aag aag ctt tgg gac tat gat ctt gca      466
Leu Ser Arg Glu Glu Ile Trp Lys Lys Leu Trp Asp Tyr Asp Leu Ala
             85                  90                  95 act gtt atc gga ttc ttc ggt gtc ttt gtt tta acc gct tgt gtc tac      514
Thr Val Ile Gly Phe Phe Gly Val Phe Val Leu Thr Ala Cys Val Tyr
            100                 105                 110 ttc atg tct cgt cct cgc tct gtt tat ctt att gat ttc gct tgt tac      562
Phe Met Ser Arg Pro Arg Ser Val Tyr Leu Ile Asp Phe Ala Cys Tyr
        115                 120                 125 aag ccc tcc gat gaa cac aag gtacgtccca acttttccat agaggaaata         613
Lys Pro Ser Asp Glu His Lys
130                 135 gtctaaatta cttttaccca aaaaaaaaaa aaaaaaaaa atctaaatta agtatactta     673
agaaattata attgatttg tcaaaaaata ataattataa ttagatggat tagttgttta     733
tagggctgcc taaataaaat aaaattttgc ctttgcatgt gttacgttag taattatttt    793 tcagtatat ataaaagta attattttgc aaaaccttta gatattggtt acgtttgatt      853
taaaaccgaa tggtttcgta gaaatttgag aaagtagata acctaaaaac tccgattaaa    913
gaaaccggtt tgactatat aattttaact ggtttctgtt tcattttat tttataaaaa      973 aaacaatcca aatttacgac ctataatcaa aggagattga taggaaccgg actgataatt   1033
aaatgaagct gaatcaaacc aaacaaaagt tcatttaatt ccggtctctc tcgggtttaat  1093
```

-continued

```
ctcttttttgc attggattgg tttag gtg aca aaa gaa gag ttc ata gaa cta      1145
                              Val Thr Lys Glu Glu Phe Ile Glu Leu
                                      140                 145 gcg aga aaa tca ggg aag ttc gac gaa gag aca ctc ggt ttc aag aag      1193
Ala Arg Lys Ser Gly Lys Phe Asp Glu Glu Thr Leu Gly Phe Lys Lys
            150                 155                 160 agg atc tta caa gcc tca ggc ata ggc gac gag aca tac gtc cca aga      1241
Arg Ile Leu Gln Ala Ser Gly Ile Gly Asp Glu Thr Tyr Val Pro Arg
            165                 170                 175 tcc atc tct tca tca gaa aac ata aca acg atg aaa gaa ggt cgt gaa      1289
Ser Ile Ser Ser Ser Glu Asn Ile Thr Thr Met Lys Glu Gly Arg Glu
        180                 185                 190 gaa gcc tct aca gtg atc ttt gga gca cta gac gaa ctc ttc gag aag      1337
Glu Ala Ser Thr Val Ile Phe Gly Ala Leu Asp Glu Leu Phe Glu Lys
    195                 200                 205 aca cgt gta aaa cct aaa gac gtt ggt gtc ctt gtg gtt aac tgt agc      1385
Thr Arg Val Lys Pro Lys Asp Val Gly Val Leu Val Val Asn Cys Ser
210                 215                 220                 225 att ttc aac ccg aca ccg tcg ttg tcc gca atg gtg ata aac cat tac      1433
Ile Phe Asn Pro Thr Pro Ser Leu Ser Ala Met Val Ile Asn His Tyr
                230                 235                 240 aag atg aga ggg aac ata ctt agt tac aac ctt gga ggg atg gga tgt      1481
Lys Met Arg Gly Asn Ile Leu Ser Tyr Asn Leu Gly Gly Met Gly Cys
            245                 250                 255 tcg gct gga atc ata gct att gat ctt gct cgt gac atg ctt cag tct      1529
Ser Ala Gly Ile Ile Ala Ile Asp Leu Ala Arg Asp Met Leu Gln Ser
            260                 265                 270 aac cct aat agt tat gct gtt gtt gtg agt act gag atg gtt ggg tat      1577
Asn Pro Asn Ser Tyr Ala Val Val Val Ser Thr Glu Met Val Gly Tyr
        275                 280                 285 aat tgg tac gtg gga agt gac aag tca atg gtt ata cct aat tgt ttc      1625
Asn Trp Tyr Val Gly Ser Asp Lys Ser Met Val Ile Pro Asn Cys Phe
290                 295                 300                 305 ttt agg atg ggt tgt tct gcc gtt atg ctc tct aac cgt cgt cgt gac      1673
Phe Arg Met Gly Cys Ser Ala Val Met Leu Ser Asn Arg Arg Arg Asp
                310                 315                 320 ttt cgc cat gct aag tac cgt ctc gag cac att gtc cga act cat aag      1721
Phe Arg His Ala Lys Tyr Arg Leu Glu His Ile Val Arg Thr His Lys
            325                 330                 335 gct gct gac gac cgt agc ttc agg tttcattcat tttggtatta attcgtttta    1775
Ala Ala Asp Asp Arg Ser Phe Arg
            340                 345 caatctcttg accgacctag taactaattt tgtgtggttt ttagg agt gtg tac cag    1832
                                              Ser Val Tyr Gln gaa gaa gat gaa caa gga ttc aag ggg ttg aag ata agt aga gac tta      1880
Glu Glu Asp Glu Gln Gly Phe Lys Gly Leu Lys Ile Ser Arg Asp Leu
350                 355                 360                 365 atg gaa gtt gga ggt gaa gct ctc aag aca aac atc act acc tta ggt      1928
Met Glu Val Gly Gly Glu Ala Leu Lys Thr Asn Ile Thr Thr Leu Gly
                370                 375                 380 cct ctt gtc cta cct ttc tcc gag cag ctt ctc ttc ttt gct gct ttg      1976
Pro Leu Val Leu Pro Phe Ser Glu Gln Leu Leu Phe Phe Ala Ala Leu
            385                 390                 395 ctc cgc cga aca ttc tca cct gct gcc aaa acg tcc aca acc act tcc      2024
Leu Arg Arg Thr Phe Ser Pro Ala Ala Lys Thr Ser Thr Thr Thr Ser
            400                 405                 410 ttc tct act tcc gcc acc gca aaa acc aat gga atc aag tct tcc tct      2072
Phe Ser Thr Ser Ala Thr Ala Lys Thr Asn Gly Ile Lys Ser Ser Ser
    415                 420                 425
```

-continued

| | |
|---|---|
| tcc gat ctg tcc aag cca tac atc ccg gac tac aag ctc gcc ttc gag<br>Ser Asp Leu Ser Lys Pro Tyr Ile Pro Asp Tyr Lys Leu Ala Phe Glu<br>430                   435                 440                 445 | 2120 |
| cat ttt tgc ttc cac gcg gca agc aaa gta gtg ctt gaa gag ctt caa<br>His Phe Cys Phe His Ala Ala Ser Lys Val Val Leu Glu Glu Leu Gln<br>               450                     455                  460 | 2168 |
| aag aat cta ggc ttg agt gaa gag aat atg gag gct tct agg atg aca<br>Lys Asn Leu Gly Leu Ser Glu Glu Asn Met Glu Ala Ser Arg Met Thr<br>465                               470                        475 | 2216 |
| ctt cac agg ttt gga aac act tct agc agt gga atc tgg tat gag ttg<br>Leu His Arg Phe Gly Asn Thr Ser Ser Ser Gly Ile Trp Tyr Glu Leu<br>         480                     485                     490 | 2264 |
| gct tac atg gag gcc aag gaa agt gtt cgt aga ggc gat agg gtt tgg<br>Ala Tyr Met Glu Ala Lys Glu Ser Val Arg Arg Gly Asp Arg Val Trp<br>495                   500                 505 | 2312 |
| cag atc gct ttc ggt tct ggt ttt aag tgt aac agt gtg gtg tgg aag<br>Gln Ile Ala Phe Gly Ser Gly Phe Lys Cys Asn Ser Val Val Trp Lys<br>510                   515                 520                 525 | 2360 |
| gca atg agg aag gtg aag aag cca acc agg aac aat cct tgg gtg gat<br>Ala Met Arg Lys Val Lys Lys Pro Thr Arg Asn Asn Pro Trp Val Asp<br>               530                     535                  540 | 2408 |
| tgc atc aac cgt tac cct gtg cct ctc taa attatcattc ttctaaatta<br>Cys Ile Asn Arg Tyr Pro Val Pro Leu<br>         545                     550 | 2458 |
| aatcaagtaa gatctctaat tactccaacc aaaagataca gtttggttgg atgataggag | 2518 |
| ttatttactg atcattcgta tctaagtctg ttataagaat ggatgtggct agagtcctgt | 2578 |
| tcagcttcaa cttgttttat tttttgtttg ttctctattg gatcttcata aactttgaga | 2638 |
| gattaaagaa aaaactctt ctttagtttg atagaacaga tggtcattgt aatttctttta | 2698 |
| atatgtcaaa gtaaaacaat ttcttttaa ggcaatctat attcagatac ataataaatt | 2758 |
| tagtttacgt gtataagaag atac | 2782 |

<210> SEQ ID NO 2
<211> LENGTH: 550
<212> TYPE: PRT
<213> ORGANISM: Arabidopsis thaliana

<400> SEQUENCE: 2

Met Gly Arg Ser Asn Glu Gln Asp Leu Leu Ser Thr Glu Ile Val Asn
1                   5                   10                 15

Arg Gly Ile Glu Pro Ser Gly Pro Asn Ala Gly Ser Pro Thr Phe Ser
               20                   25                   30

Val Arg Val Arg Arg Arg Leu Pro Asp Phe Leu Gln Ser Val Asn Leu
         35                     40                   45

Lys Tyr Val Lys Leu Gly Tyr His Tyr Leu Ile Asn His Ala Val Tyr
50                   55                   60

Leu Ala Thr Ile Pro Val Leu Val Leu Val Phe Ser Ala Glu Val Gly
65                   70                   75                   80

Ser Leu Ser Arg Glu Glu Ile Trp Lys Lys Leu Trp Asp Tyr Asp Leu
               85                   90                   95

Ala Thr Val Ile Gly Phe Phe Val Phe Val Leu Thr Ala Cys Val
                   100               105              110

Tyr Phe Met Ser Arg Pro Arg Ser Val Tyr Leu Ile Asp Phe Ala Cys
         115                     120                  125

Tyr Lys Pro Ser Asp Glu His Lys Val Thr Lys Glu Glu Phe Ile Glu
130                   135                   140

-continued

```
Leu Ala Arg Lys Ser Gly Lys Phe Asp Glu Glu Thr Leu Gly Phe Lys
145                 150                 155                 160

Lys Arg Ile Leu Gln Ala Ser Gly Ile Gly Asp Glu Thr Tyr Val Pro
                165                 170                 175

Arg Ser Ile Ser Ser Ser Glu Asn Ile Thr Thr Met Lys Glu Gly Arg
            180                 185                 190

Glu Glu Ala Ser Thr Val Ile Phe Gly Ala Leu Asp Glu Leu Phe Glu
        195                 200                 205

Lys Thr Arg Val Lys Pro Lys Asp Val Gly Val Leu Val Asn Cys
210                 215                 220

Ser Ile Phe Asn Pro Thr Pro Ser Leu Ser Ala Met Val Ile Asn His
225                 230                 235                 240

Tyr Lys Met Arg Gly Asn Ile Leu Ser Tyr Asn Leu Gly Gly Met Gly
                245                 250                 255

Cys Ser Ala Gly Ile Ile Ala Ile Asp Leu Ala Arg Asp Met Leu Gln
                260                 265                 270

Ser Asn Pro Asn Ser Tyr Ala Val Val Val Ser Thr Glu Met Val Gly
            275                 280                 285

Tyr Asn Trp Tyr Val Gly Ser Asp Lys Ser Met Val Ile Pro Asn Cys
290                 295                 300

Phe Phe Arg Met Gly Cys Ser Ala Val Met Leu Ser Asn Arg Arg Arg
305                 310                 315                 320

Asp Phe Arg His Ala Lys Tyr Arg Leu Glu His Ile Val Arg Thr His
                325                 330                 335

Lys Ala Ala Asp Asp Arg Ser Phe Arg Ser Val Tyr Gln Glu Glu Asp
                340                 345                 350

Glu Gln Gly Phe Lys Gly Leu Lys Ile Ser Arg Asp Leu Met Glu Val
        355                 360                 365

Gly Gly Glu Ala Leu Lys Thr Asn Ile Thr Thr Leu Gly Pro Leu Val
370                 375                 380

Leu Pro Phe Ser Glu Gln Leu Leu Phe Phe Ala Ala Leu Leu Arg Arg
385                 390                 395                 400

Thr Phe Ser Pro Ala Ala Lys Thr Ser Thr Thr Thr Ser Phe Ser Thr
                405                 410                 415

Ser Ala Thr Ala Lys Thr Asn Gly Ile Lys Ser Ser Ser Ser Asp Leu
                420                 425                 430

Ser Lys Pro Tyr Ile Pro Asp Tyr Lys Leu Ala Phe Glu His Phe Cys
        435                 440                 445

Phe His Ala Ala Ser Lys Val Val Leu Glu Glu Leu Gln Lys Asn Leu
    450                 455                 460

Gly Leu Ser Glu Glu Asn Met Glu Ala Ser Arg Met Thr Leu His Arg
465                 470                 475                 480

Phe Gly Asn Thr Ser Ser Ser Gly Ile Trp Tyr Glu Leu Ala Tyr Met
                485                 490                 495

Glu Ala Lys Glu Ser Val Arg Arg Gly Asp Arg Val Trp Gln Ile Ala
                500                 505                 510

Phe Gly Ser Gly Phe Lys Cys Asn Ser Val Val Trp Lys Ala Met Arg
        515                 520                 525

Lys Val Lys Lys Pro Thr Arg Asn Asn Pro Trp Val Asp Cys Ile Asn
530                 535                 540

Arg Tyr Pro Val Pro Leu
545                 550
```